US 6,495,593 B1

(12) United States Patent
Bagchi et al.

(10) Patent No.: US 6,495,593 B1
(45) Date of Patent: Dec. 17, 2002

(54) COMPOSITIONS FOR PREVENTING OR TREATING ADVERSE PHYSIOLOGICAL EFFECTS ASSOCIATED WITH CARDIAC DISEASE

(75) Inventors: Debasis Bagchi, Concord, CA (US); Dipak K. Das, West Hartford, CT (US)

(73) Assignee: Dry Creek Nutrition, Inc., Modesto, CA (US)

( * ) Notice: Subject to any disclaimer, the term of this patent is extended or adjusted under 35 U.S.C. 154(b) by 0 days.

(21) Appl. No.: 09/596,859

(22) Filed: Jun. 19, 2000

Related U.S. Application Data (60) Provisional application No. 60/140,296, filed on Jun. 18, 1999.

(51) Int. Cl.$^7$ ............................................. A61K 31/35
(52) U.S. Cl. ..................... 514/456; 514/183; 514/449; 514/450
(58) Field of Search ................... 514/183, 449, 514/450, 456; 549/403; 536/8; 424/195.11

(56) References Cited

U.S. PATENT DOCUMENTS

| | | | | |
|---|---|---|---|---|
| 4,698,360 | A | 10/1987 | Masquelier | 514/456 |
| 5,607,965 | A | 3/1997 | Kondo et al. | 514/456 |
| 5,762,936 | A | * 6/1998 | Ronzio et al. | 424/195.1 |
| 5,912,363 | A | 6/1999 | Nafisi-Movaghar et al. | 549/399 |
| 6,086,910 | A | 7/2000 | Howard et al. | 424/442 |
| 6,099,854 | A | 8/2000 | Howard et al. | 424/440 |

FOREIGN PATENT DOCUMENTS

| | | |
|---|---|---|
| EP | 0692480 A1 | 1/1996 |
| EP | 0713706 A2 | 5/1996 |
| FR | 1235379 | 6/1971 |
| FR | 1349483 | 4/1974 |
| WO | WO 97/39632 | 10/1997 |

OTHER PUBLICATIONS

International Search Report of Application No. EP PCT/US 00/40240, mailed Oct. 26, 2000.

Stoclet, JC. et al., "Endothelial no release caused by red wine polyphenols," *J. Physiol. Pharmacol.*, 50(4):535–40 (Dec. 1999).

Sato, M. et al., "Cardioprotective Effects of Grape Seed Proanthocyanidin Against Ischemic Reperfusion Injury," *J. Mol. Cell Cardiol.*, 31, 1289–1297 (Jun. 1999).

Das, D. et al., "Amelioration of Cardiomyocyte Apoptosis by IH636 Grape Seed Proanthocyanidin Extract Through the Inhibition of the JNK1 and cJUN," *1999 SFRR Europe Winter Meeting*, OP26 (Dec. 2, 1999).

Sato, M. et al., "Peroxyl and Hydroxyl Radical Scavenging Activities of Polyphenolic Components Play a Role in Cardioprotective Effects of Red Wine," *The FASEB Journal*, vol. 13, No. 7, 609 (Apr. 23, 1999).

Sato, M, et al., "Cardioprotective Effects of a Novel IH636 Grape Seed Proanthocyanidin Extract," *IX Biannual Meeting International Society for Free Radical Research*, PS 15–60 (Sep. 7, 1998).

Wong, V. et al., "Antioxidant Grape Seed Proanthocyanidin Extract (GSPE) and a DNA Repair Modulator 3–Aminobenzamide (3–AB) Protect Doorubicin (DOX)–Induced Cardiotoxicity in vivo," *Toxicological Sciences*, vol. 48, No. 1–S (Mar. 1999).

Sato, M, et al., "Cardioprotective Effects of a Novel IH636 Grape Seed Proanthocyanidin Extract,"*IX Biannual Meeting of the International Society for Free Radical Research*, vol. 34, Suppliment 1, p. 207 (Sep. 7, 1998).

Bagchi, D. et al., "Oxygen free radical scavenging abilities of vitamins C and E, and a grape seed proanthocyanidin extract in vitro," *Res. Commun. Mol. Pathol. Pharmacol.*, 95(2) 179–89 (Feb. 1997).

Bagchi, D. et al., "Protective effects of grape seed proanthocyanidins and selected antioxidants against TPA–induced hepatic and brain lipid peroxidation and DNA fragmentation, and peritoneal macrophage activation in mice," *Gen. Pharmacol.*, 30(5) 771–6 (May 1998).

Bagchi, D. et al., "Smokeless tobacco, oxidative stress, apoptosis, and antioxidants in human oral keratinocytes," *Free Radic. Biol. Med.*, 26(7–8):992–1000 (Apr. 1999).

Tyson, D. et al., "Acute Effects of Grape Seed Extract and Niacin–Bound Chromium on Cardiovascular Parameters of Normotensive and Hypertensive Rats," *Research Communications in Pharmacology and Toxicology*, vol. 5, Nos. 1 & 2: 91–106 (Sep. 5, 2000).

Das, D. et al., "Cardioprotection of Red Wine: Role of Polyphenolic Antioxidants" *Drugs Exptl. Clin. Res.* XXV(2/3): 115–120 (May 20, 1999).

* cited by examiner

*Primary Examiner*—Carla J. Myers
(74) *Attorney, Agent, or Firm*—Marshall, Gerstein & Borun

(57) ABSTRACT

A method is disclosed for preventing or treating the adverse physiological effects associated with cardiac disease by administering a purified proanthocyanidin composition to the person in an amount effective to prevent or reduce the adverse physiological effects.

1 Claim, 7 Drawing Sheets

COMPOSITIONS FOR PREVENTING OR TREATING ADVERSE PHYSIOLOGICAL EFFECTS ASSOCIATED WITH CARDIAC DISEASE

This application claims priority on U.S. Provisional Patent Application Serial No. 60/140,296 filed Jun. 18, 1999, the disclosure of which is hereby incorporated by reference.

BACKGROUND OF THE INVENTION

The invention relates generally to a method and composition for preventing and/or treating adverse physiological effects associated with cardiac disease.

Heart disease is one of the most common forms of disease in many parts of the world. and is a leading cause of mortality and morbidity. Heart disease may be characterized as either chronic or acute. Chronic cardiac disease includes cardiomyopathies, congestive heart failure and conditions such as chronic pericardial disease. Cardiomyopathies are characterized hemodynamically into dilated, hypertrophic, restrictive and obliterative cardiomyopathy and can be of known or idiopathic etiology. Among the etiologies of dilated cardiomyopathy are pregnancy, drugs and toxins, such as alcohol, cocaine and chemotherapeutic agents and infectious and autoimmune processes. Hypertrophic cardiomyopathy is hereditary in more than 50% of cases and has a distinctive pattern of myocardial hypertrophy (thickening of muscle). Restrictive cardiomyopathies are usually the product of an infiltrative disease of the myocardium, such as amyloidosis, hemochromatosis or a glycogen storage disease, and may also be seen in certain diabetic patients. Obliterative cardiomyopathy can be caused by endomyocardial fibrosis and hypereosinophilis syndrome.

Congestive heart failure is characterized by the inability of the heart to deliver a supply of oxygenated blood sufficient to meet the metabolic needs of peripheral tissues at normal filling pressures and is a common complication of cardiomyopathies and is also a complication of other conditions such as diabetes mellitus, coronary artery disease, myocarditis, aortic stenosis, pericarditis, neoplastic pericardial effusion and numerous other conditions.

Acute cardiac diseases include acute pericarditis as well as complications of myocardial infarction and the ischemia resulting therefrom. One such complication is the injury resulting from the physiological effects resulting from reperfusion of the ischemic tissue. Ischemia is defined as a condition in which a tissue or organ does not receive a sufficient supply of blood, usually due to obstruction of the arterial blood supply. Ischemic reperfusion injury describes functional, metabolic, or structural changes in ischemic heart muscle thought to result from reperfusion of oxygenated blood to the ischemic areas. These changes can be fatal to muscle cells, and can include edema with explosive cell swelling and disintegration, sarcolemma disruption, fragmentation of mitochondria, contraction band necrosis, enzyme washout, and calcium overload. Other damage can include hemorrhage and ventricular arrhythmias.

Myocardial cellular injury associated with the reperfusion of ischemic myocardium has been attributed to many interrelated factors, including intracellular $Ca^{2-}$ overloading, loss of sarcolemmal phospholipids and oxygen free radical generation (Bagchi et al., "Interrelationship Between Cellular Calcium Homeostasis and Free Radical Generation in Mycocardial Reperfusion Injury, Chem. Biol. Int., 104:65–85 (1997)). In particular, such injury can occur when a person is provided with certain compounds, such as an artificial blood substitute. One possible mechanism of damage for ischemic reperfusion injury is via oxygen free radicals. Reactive oxygen species have been implicated in pathogenesis of diverse degenerative diseases including ischemic heart disease (Belch et al., "Oxygen Free Radicals and Congestive Heart Failure," Brit. Heart J., 65:245–248 (1991); Singal et al., "Role of Free Radicals in Catecholamine-Induced Cardiomyopathy," Can. J. Physiol. Pharmacol., 60:1390–1397 (1982); Otani et al., "Enhanced prostaglandin synthesis due to phospholipase breakdown in ischemic-reperfused myocardium. Control of its production by a phospholipase inhibitor or free radical scavengers., "J. Mol. Cell Cardiol., 18:953–961 (1986); Steinbrecher et al., "Role of Oxidatively Modified LDL in Atherosclerosis, Free Rad. Biol. Med., 9:155–168 (1990)). Evidence exists that oxidative stress resulting from increased production of free radicals associated with decreased amount of antioxidants in the myocardium plays a crucial role in ischemic heart disease, as well as atherosclerosis, congestive heart failure, cardiomyopathy, hypertrophy and arrhythmias (Das et al., "Protection Against Free Radical Injury in the Heart and Cardiac Performance," Exercise and Oxygen Toxicity, (C. K. Sen, L. Packer, O. Hanninen, eds.) Elsevier Science, Amsterdam (1995). Epidemiological relationships also exist between oxidative stress and occurrence of cardiovascular diseases that include ischemic heart disease (Gey et al., "Inverse Correlation Between Plasma Vitamin E and Mortality From Ischemic Heart Disease in Cross-Cultural Epidemiology," Am. J. Clin. Nutr., 53:3265–3345 (1991)) and arteriosclerosis (Gey, "On the Antioxidant Hypothesis With Regard to Arteriosclerosis," Bibl. Nutr. Dieta., 37:53–91 (1986)). The anticipation of free radicals has been demonstrated by the beneficial effects of antioxidants and antioxidant enzymes (Otani et al., "Cardiac Performance During Reperfusion Improved by Pretreatment With Oxygen Free Radical Scavengers," J. Thoracic Cardiovasc. Surg., 91:290–295 (1986)) and free radical scavengers (Arroyo et al., "Identification of Free Radicals in Myocardial Ischemia/Reperfusion by Spin Trapping With Nitrone DMPO, FEBS Lett., 221:101 –104 (1987)). The role of oxygen free radicals in myocardial ischemic reperfusion injury is well documented. The presence of hydroxyl (OH—) and other reactive oxygen species has been demonstrated directly using ESR and High Pressure Liquid Chromatography (HPLC) techniques (Tosaki et al., "Comparisons of ESR and HPLC methods for the detection of hydroxyl radicals in ischemic/reperfused hearts. A relationship between the genesis of oxygen-free radicals and reperfusion-induced arrhythmias, Biochem. Pharmacol., 45:961–969 (1993)) and indirectly by identifying the formation of malonaldehyde (Cordis et al., "Detection of Oxidative Stress in Heart by Estimating the Dinitrophenylhydrazine Derivative of Malonaldehyde," J. Mol. Cell. Cardiol., 27:1645–1653 (1995)) and 8-hydroxydeoxyguanosine (Cordis et al., "Detection of Oxidative DNA Damage to Ischemic Reperfused Rat Hearts by 8-Hydroxydeoxyguanosine Formation," Mol. Cell. Cardiol., 30:1939–1944 (1998)) in the heart as well as in the coronary effluents.

Ischemic reperfusion injury is thought to be prevented by warm blood cardioplegic infusion prior to reperfusion. Additionally, pretreatment of hearts with antioxidants or antioxidant enzymes can ameliorate ischemic reperfusion injury, presumably by reducing the formation of detrimental free radicals (Das et al., "Evaluation of Antioxidant Effectiveness in Ischemia Reperfusion Tissue Injury Methods,"

*Methods Enzymol.*, 233: 601–610 (1994); Jayakumari et al., "Antioxidant Status in Relation to Free Radical Production During Stable and Unstable Anginal Syndromes," *Atherosclerosis*, 94:183–190 (1992)). Nevertheless, the administration of traditional antioxidant compositions has not necessarily proved to be completely effective in the prevention or treatment of the adverse physiological effects associated with cardiac disease generally or ischemic reperfusion injury in particular. There thus remains a need for an effective method to prevent and/or treat ischemic reperfusion injury in persons who have or are at risk for ischemic reperfusion injury.

Proanthocyanidins comprise a group of polyphenolic bioflavonoids ubiquitously found in fruits and vegetables. They are the most common type of tannins found in fruits and vegetables, and are present in high amounts in the seeds and skins of grapes. Proanthocyanidins have been the subject of considerable interest because of their broad pharmacologic activity and therapeutic potential (Chen et al., "Antioxidative Activity of Natural Flavonoids is Governed by Number and Location of Their Aromatic hydroxyl Groups, *Chem. Phys. Lipids*, 79:157–163 (1996)). The biological and medicinal properties of the proanthocyanidins have been extensively reviewed (Rice-Evans et al., "Structure-Antioxidant Activity Relationships of Flavonoids and Phenolic Acids," *Free Rad. Biol. Med.*, 20:933–956 (1996)). For example, the epidemiological evidence indicates that the consumption of red wine is beneficial in the prevention of coronary heart disease (Rimm et al., "Prospective Study of Alcohol Consumption and Risk of Coronary Disease in Men," *Lancet*, 338:464–86 (1991); St. Leger et al., "Factors Associated With Cardiac Mortality in Developed Countries With Particular Reference to the Consumption of Wine," *Lancet*, 1:1017–1020 (1979)). This beneficial effect has been attributed to the antioxidants present in the polyphenol fraction of red wine (Hertog et al., "Antioxidant Flavonols and Coronary Heart Disease Risk," *Lancet*, 349:699 (1997)), such as the proanthocyanidins present in grape seeds. Also, a Dutch epidemiological study showed that incidence of coronary heart disease in elderly males is inversely correlated with their intake of flavonoids (Hertog et al., "Dietary Antioxidant Flavonoids and Risk of Coronary Heart Disease: The Zutphen Elderly Study," *Lancet*, 342:1007–1011 (1993)), further supporting cardioprotective effects of polyphenolic compounds.

Proanthocyanidins and other polyphenolic bioflavonoids have demonstrated potential antioxidant and free radical scavenging ability, and have demonstrated a broad spectrum of biological, pharmacological and medicinal properties. Proanthocyanidins consist of polymers of the flavan-3-ol units (+)-catechin, (−)-epicatechin and (−)-epicatechin 3-O-gallate linked by C4–C8 or C4–C6 bonds. Some proanthocyanidins carry galloyl residues linked to the C-3 alcoholic function of the flavan-3-ol units.

Proanthocyanidins are present in a number of natural plant sources and are particulary plentiful in the tissue and seeds of various fruits. The skins and seeds of grapes (*Vitis vinifera*) are particulary rich sources of proanthocyanidins with red wine and grape juice having high contents of proanthocyanidins. (See U.S. Pat. Nos. 5,484,594 and 5,912,363 describing methods for extraction of purified proanthocyanidin compositions.) A purified proanthocyanidin composition derived from grape seeds according to such methods contains monomeric, dimeric, trimeric, tetrameric and higher oligomeric and polymeric proanthocyanidins, as well as tannin. According to U.S. Pat. No. 4,698,360 the bark of certain species of maritime pine has also proved to be a rich source of proanthocyanidins.

Proanthocyanidins are known to be potent free radical scavengers and metal chelators and reduce free radicals, a by-product of metabolism and block their propagation. The proanthocyanidins are also thought to protect cells from lipid peroxidation, resulting in the protection of target organs' membranes. One example, is the protection of low density lipoproteins (LDL) from oxidation. While the oxidation of LDL has been identified as a contributing factor to atherosclerosis and cardiovascular disease, the ability of proanthocyanidin compositions to prevent or treat specific adverse physiological effects of cardiac disease has not been demonstrated.

SUMMARY OF THE INVENTION

The present invention provides methods for preventing and treating the adverse physiological effects associated with cardiac disease by the administration of purified proanthocyanidin compositions. Specifically, the invention provides a method of preventing or treating adverse physiological effects associated with cardiac disease in a person at risk for such adverse physiological effects, the method comprising: identifying a person at risk for such adverse physiological effects; and administering a purified proanthocyanidin composition to the person in an amount effective to prevent or reduce the adverse physiological effects.

Cardiac disease susceptible to treatment according to the present method includes both chronic and acute cardiac disease. Chronic cardiac diseases, having physiological effects susceptible to treatment according to the invention include but are not limited to cardiomyopathies, congestive heart failure and conditions such as chronic pericardial disease. Acute cardiac diseases susceptible to treatment according to the present method include, but are not limited to, ischemia reperfusion injury resulting from myocardial infarction, administration of blood substitutes, circulatory collapse from hemorrhage and the like as well as conditions such as acute peritonitis and other acute cardiac conditions.

The present invention is based upon the discovery that administration of sufficient dosages of purified proanthocyanidin compositions to a human or mammalian subject alleviates adverse physiological effects associated with cardiac disease including decreased cardiac pressure, decreased aortic flow, decreased systolic aortic pressure, and enhancement of the proapoptotic factors, c-Jun and JNK 1 in the heart tissue. In particular, it is believed that the enhancement of the proapoptotic factors c-Jun and JNK-1 associated with apoptosis (programmed cell death) may be one mechanism by which various adverse physiological effects of cardiac disease are mediated. The decreased enhancement of these proapoptotic factors upon administration of the purified proanthocyanidin compositions of the invention may thus be the mechanism by which ischemia reperfusion injury and other cardiac diseases are prevented and treated by administration of purified proanthocyanidin compositions.

The compositions of the invention may be administered prophylactically or therapeutically in treatment of chronic cardiac disease conditions. Alternatively, they may be administered prophylactically in anticipation of a acute cardiac event such as in preparation for cardiac surgery such as angioplasty and the like or other surgery having potential hemodynamic effects upon the heart. Further, the purified proanthocyanidin compositions of the invention may be administered in response to acute cardiac events such as myocardial infarction and events resulting therefrom such as ischemia reperfusion of the heart muscle.

The present invention also provides a composition comprising purified proanthocyanidin composition and another compound, the introduction of which into a person's body can lead to such injury, such as an artificial blood substitute. Artificial blood substitutes to which purified proanthocyanidin compositions of the invention may be usefully applied according to this aspect of the invention include perfluorocarbon emulsions available commercially as FLUOSOL® (Green Cross Corporation, Japan) and OXYGENT® (Alliance Pharmaceutical Corp., San Diego Calif.).

Also provided by the invention is use of a purified proanthocyanidin composition in preparation of a medicament for prevention or treatment of adverse physiological effects associated with cardiac disease.

Purified proanthocyanidin compositions of the invention may be isolated or derived from a variety of plant sources according to known methods or may be produced synthetically. Proanthocyanidins are found in the fruit and seeds of a wide variety of fruit plants including but not limited to strawberry, blueberry and grapes. Proanthocyanidins are also present in large quantities in maritime pine bark, oak wood, black and green tea and in cocoa powder. A preferred source for proanthocyanidins is grapes with grape skin and particularly grape seeds being preferred sources. Purified proanthocyanidin compositions may be obtained by practice of methods such as those described in Nasfi-Movaghar et al., U.S. Pat. No. 5,912,363 the disclosure of which is hereby incorporated by reference. A particularly preferred purified proanthocyanidin composition available as a standardized water-ethanol extract from red grape seeds for use according to the invention is available as a grape seed proanthocyanidin extract (GSPE) known as ActiVin® available from InterHealth Nutraceuticals Inc., Concord, Calif. A compositional analysis of the ActiVin® grape seed proanthocyanidin extract shows a content comprising (by weight) 54% proanthocyanidin dimer, 13% proanthocyanidin trimer, 7% proanthocyanidin tetramer, and 6% monomer and other flavonoids. Because it is believed that the prophylactic and therapeutic activities of the purified proanthocyanidin compositions of the invention are primarily associated with the low molecular weight ($DP_2$ to $DP_4$) oligomeric content of the purified proanthocyanidin compositions preferred purified proanthocyanidin compositions comprise at least 50% and more preferably greater than 70% by weight $DP_2$ to $DP_4$ oligomeric proanthocyanidins.

While it is contemplated that daily dosages of the purified proanthocyanidin compositions of the invention can range up to 1000 mg/day and higher, it is recognized that the ability of the human body to absorb and retain large quantities of proanthocyanidins may be limited. Nevertheless, it may be desirable in cases of acute cardiac disease to administer dosages of 1000 mg/day and larger intravenously and otherwise by injection (intramuscularly) to maximize the immediate therapeutic or prophylactic effect of the proanthocyanidins. More conventionally, and particularly in cases of administration for prophylactic uses the invention contemplates administering dosages ranging from 50 to 200 mg/day for adult persons. According to one preferred method of the invention, the purified proanthocyanidin composition is administered twice daily orally soon after the person has eaten a meal.

Other features and advantages of the present invention should become apparent from the following detailed description of the invention, taken with the illustrative drawings, which illustrate the principles of the invention.

BRIEF DESCRIPTION OF THE DRAWINGS

FIG. 4A is from the control group, and FIG. 4B are from the proanthocyanidin group.

DETAILED DESCRIPTION OF THE INVENTION

The present invention involves administering purified proanthocyanidin composition to a person who has suffered or is at risk to suffer, adverse effects of chronic or acute cardiac disease. The present invention also involves a composition comprising purified proanthocyanidin composition and another compound, the introduction of which into a person's body can lead to such injury, such as an artificial blood substitute. The invention also provides use of a purified proanthocyanidin composition in preparation of a medicament for prevention or treatment of adverse physiological effects associated with cardiac disease including ischemic reperfusion.

According to one aspect of the invention, post-ischemic ventricular recovery was compared between two groups of rat hearts, a purified proanthocyanidin composition-fed group and control group. The results of the study demonstrated that the hearts of rats fed purified proanthocyanidin composition (grape seed proanthocyanidin extract, ActiVin®, Interhealth Nutraceuticals) displayed an increased tolerance to ischemia reperfusion injury and significantly reduced infarct size. In vitro studies showed that purified proanthocyanidin composition is a potent scavenger of peroxyl and hydroxyl radicals that are generated in the ischemic reperfused myocardium, suggesting that cardioprotective properties may be attributed, at least in part, to the hydroxyl and peroxyl radicals scavenging activities of purified proanthocyanidin composition.

The present invention resides in a method to prevent and/or reduce the effect of the adverse physiological effects of cardiac disease by administering purified proanthocyanidin composition to a person identified to be at risk for such injury in an amount effective to prevent or reduce the injury. The invention also provides a composition comprising purified proanthocyanidin composition and a compound which, if introduced into a person's body, can lead to such injury, such as an artificial blood substitute. In one study, postischemic ventricular recovery was compared between two groups of rat hearts, a purified proanthocyanidin composition-fed group and a control group. The results of the study demonstrated that purified proanthocyanidin composition-fed rat hearts displayed an increased tolerance to ischemia reperfusion injury and significantly reduced infarct size. Additionally, in vitro studies showed that a purified proanthocyanidin composition is a potent scavenger of peroxyl and hydroxyl radicals that are generated in the ischemic reperfused myocardium, suggesting that cardioprotective properties may be attributed, at least in part, to the hydroxyl and peroxyl radicals scavenging activities of purified proanthocyanidin composition. The results of the studies indicate that use of purified proanthocyanidin compositions to prevent or treat cardiac disease including cardiac ischemic reperfusion injury is a potentially more effective method that those methods previously known to the art.

EXAMPLE

According to this example, male Sprague-Dawley rats weighing 275–300 g were provided with food and water ad libitum up until the start of the experimental procedure. Rats were randomly assigned to one of two groups, Control or Proanthocyanidin. Half of the rats were fed grape seed proanthocyanidin extract (GSPE) (100 mg/kg/day for three weeks) (ActiVin®: Batch # 609016, InterHealth Nutraceuticals, Concord, Calif.) orally in water, while the other half were given water only. All other chemicals used in this study were obtained from Sigma Chemical Co. (St. Louis, Mo.), unless otherwise specified.

Experimental Design

Rats were anesthetized with Sodium Pentobarbital (80 mg/kg b.w., i.p. injection, Abbott Laboratories, North Chicago, Ill.), and anticoagulated with Heparin Sodium (500 IU/kg b.w., i.v. injection, Elkins-Sinn Inc., Cherry Hill, N.J.). After ensuring sufficient depth of anesthesia, thoracatomy was performed, and the hearts were excised and immersed in ice-cold perfusion buffer. Aortic cannulation was performed as quickly as possible and hearts were perfused in the retrograde Langendorff mode at a constant perfusion pressure of 100 cm $H_2O$ (Engelman et al., 1995).

The perfusion buffer used in this example consisted of a modified Krebs-Henseleit bicarbonate buffer (KHB) (in mM: 118 NaCl, 4.7 KCl, 1.2 $MgSO_4$, 1.2 $KH_2PO_4$, 7.5 $NaHCO_3$, 10 glucose and 1.7 $CaCl_2$, gassed with 95% $O_2$–5% CO filtered through a 5 $\mu$m filter to remove any particulate contaminants, pH 7.4). The buffer was maintained at a constant temperature of 37° C., and was gassed continuously for the duration of the experiment. Left atrial cannulation was then carried out, and after allowing for a stabilization period of 10 minutes in the retrograde perfusion mode, the circuit was switched to the antegrade working mode, which allows for the measurement of myocardial contractility as well as aortic and coronary flows, as described in detail in a previous paper (Engelman et al., "Hypoxic Preconditioning Preserves Antioxidant Reserve in the Working Rat Heart," *Cardiovasc. Res.*, 29:133–140 (1995)). This essentially is a left heart preparation, in which the heart is perfused at a constant preload of 17 cm $H_2O$ (being maintained by means of a Masterflex variable speed modular pump, Cole Parmer Instrument Company, Vernon Hills, Ill.) and pumps against an afterload of 100 cm $H_2O$.

At the end of 10 minutes, after the attainment of steady-state cardiac function, baseline functional parameters were recorded and coronary effluent samples were collected for biochemical assays. Hearts were then subjected to global ischemia for 30 minutes followed by 2 hours of reperfusion. The first 10 minutes of reperfusion were in the retrograde mode to allow for postischemic stabilization, and thereafter in the antegrade working mode to allow for assessment of functional parameters. These parameters were recorded at 30 minutes, 60 minutes and 120 minutes into reperfusion.

Cardiac Functional Assessment

Aortic pressure was measured using a Gould P23XL pressure transducer (Gould Instrument Systems Inc., Valley View, Ohio) connected to a side arm of the aortic cannula. The signal was amplified using a Gould 6600 series signal conditioner (Gould Instrument Systems Inc., Valley View, Ohio) and monitored on a CORDAT II real-time data acquisition and analysis system (Triton Technologies, San Diego, Calif.). Heart rate, developed pressure (defined as the difference of the maximum systolic and diastolic aortic pressures) and the first derivative of developed pressure were all derived or calculated from the continuous pressure signal. Aortic flow was measured using a calibrated flowmeter (Gilmont Instruments Inc.), and coronary flow was measured by timed collection of the coronary effluent dripping from the heart.

Infarct Size Estimation

At the end of each experiment, the heart was excised, and the left ventricle was removed and sliced into cross-sectional pieces of 1 mm, which were weighed. All of the pieces were incubated for 20 min with 1% triphenyl tetrazolium stain (TTC) in 100 mM phosphate buffer (pH 7.4) at 37° C. (Schultz et al., "Glibenclamide-Induced Blockade of Ischemic Preconditioning is Time Dependent in Intact Rat Heart," *Am. J. Physiol.*, 272:H2607–2615 (1997)). Each slice was scanned with a computer-assisted scanner (ScanJet 5p, Hewlett-Packard). The entire area at risk, i.e., the risk zone, was indicated by the whole ventricle stained in red by TTC, while the infarct zone was unstained by TTC. These were measured using computerized planimetry software (NIH Image 1.61). These areas were multiplied by the weight of each slice, and the results summed to obtain the weight of the risk zone and the infarct zone. Infarct size was expressed as the ratio of the infarct zone to the risk zone.

Malonaldehyde Assay

The production of malonaldehyde (MDA) is an index of the occurrence of lipid peroxidation and the development of oxidative stress. MDA was assayed as described previously (Cordis et al., "Detection of Oxidative Stress in Heart by Estimating the Dinitrophenylhydrazine Derivative of Malonaldehyde," *J. Mol. Cell. Cardiol.*, 27:1645–1653 (1995)) to monitor the development of oxidative stress during ischemia reperfusion. Coronary perfusates were collected at the time of recording baseline functional parameters and thereafter at timepoints of 10 min, 30 min, and 120 min into reperfusion for the measurement of MDA. The MDA in the collected coronary perfusate samples was derivatized using 2,4-dinitrophenylhydrazine (DNPH). 2 mL of perfusate was added to 0.1 mL of DNPH reagent (310 mg DNPH in 100 mL 2N HCl, 1.56 mmol DNPH) in a 20 mL Teflon lined screw-capped test tube. The contents of the tube were vortexed, and 10 mL of pentane was added prior to intermittent rocking of the tube and contents for 30 minutes. The aqueous phase was extracted 3 times with pentane, blown down with $N_2$ and reconstituted in 200 µL of acetonitrile. Aliquots of 25 µL in acetonitrile was injected onto a Beckman Ultrasphere C18 (3 mm) column in a Waters HPLC. The products were eluted isocratically with a mobile phase containing acetonitrile-$H_2O$—$CH_3COOH$ (34:66:0.1. v/v/v) and detected at three different wavelengths of 307 nm, 325 nm and 356 nm. The peak for malonaldehyde was identified by co-chromatography with a DNPH derivative of the authentic standard, peak addition, comparison of the UV patterns of absorption at the three wavelengths, and by GC-MS. The amount of MDA was quantitated by performing peak area analysis using the Maxima software program (Waters) and expressed in pmol/mL.

In Vitro Peroxyl Radical Scavenging Assay

Peroxyl radical scavenging activity was examined by adding proanthocyanidin to a peroxyl radical generating system (Makrigiorgos et al., "Novel Fluorescein-Based Flow Cytometric Method for Detection of Lipid Peroxidation," *Free Rad. Biol. Med.*, 22:93–100 (1997)). Peroxyl radicals were generated by dissolving 2,2'-azobis (2-amidinopropane) dihydrochloride (AAPH) in phosphate buffered saline (PBS) at 37° C. Scavenging activity of proanthocyanidin was compared with trolox (100 µM), a known peroxyl radical scavenger. Proanthocyanidin (10 µg/mL) or trolox (25 µg/mL) were added to the peroxyl radical generating system (final concentration of AAPH was 2 mM), and the decrease in fluorescence of 5-/6carboxyfluorescein (5-/6-CF) as a function of time (up to 1 hr) was observed at excitation and emission wavelengths of 500 and 520 nm, respectively, using a Perkin Elmer LS 50 B fluorescence spectrometer (Perkin Elmer, Norwalk, Conn.).

In Vitro Hydroxyl Radical Scavenging Assay

Aqueous solution of coumarin-3-carboxylic acid (CCA) was diluted in PBS buffer, pH 7.4 to give a final concentration of $10^{-5}$ M. Polymethylmethacrylate cuvettes containing 2.5 mL CCA solution were irradiated with $^{137}$Cs γ-ray (dose rate 1.14 Gy/min) (MDS Nordian., Ontario, Canada) at room temperature. Upon irradiation, OH radical is produced which converts CCA in aqueous solution into highly fluorescent 7-hydroxy-coumarin-3-carboxylic acid. Fluorescence was measured at room temperature with a Perkin Elmer LS 50 fluorimeter (excitation 400 nm, emission 450 nm) (Collins et al., "Coumarin Chemical Dosimeter for Radiation Therapy," *Med. Phys.*, 21: 1741–1747 (1994)). The OH radical scavengers like dimethyl sulfoxide (DMSO) reduced the induction of 7-OH-CCA formation indicating scavenging of OH radical. The scavenging activity of the proanthocyanidin extract was compared against 1 mM DMSO.

Statistical Analysis

The values for myocardial functional parameters, MDA, total and infarct volumes and infarct sizes were all expressed as the mean ±SEM (standard error of the mean). Differences between control and proanthocyanidin data were analyzed for significance by performing a Students t-test. The results were considered significant if the value of p was less than 0.05.

Cardiomyocytes were isolated from each heart and the degree of apoptosis (programmed cell death) was evaluated by the terminal-deoxynucleotidyl transferase (TdT) mediated dUTP biotin nick end labeling (TUNEL) method. The extent of DNA fragmentation was assessed by subjecting the DNA molecules to electrophoresis. Western blot analysis was performed to estimate the abundance of c-Jun and JNK-a proteins.

RESULTS

Cardiac Functional Assessment

Figure 1A:
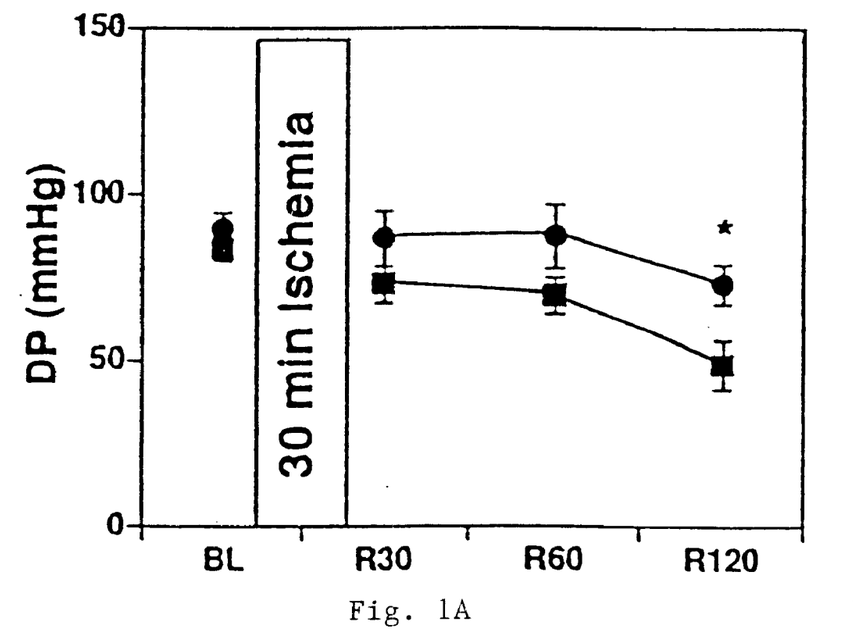
FIGS. 1A and 1B are a graphical representation of the measured developed pressure (1A) and the maximum first derivative of developed pressure (1B) for rats in the control and proanthocyanidin groups. The squares are control data points, and the circles are proanthocyanidin data points. Results are expressed as means ±SEM of six rats per group.
Figure 1B:
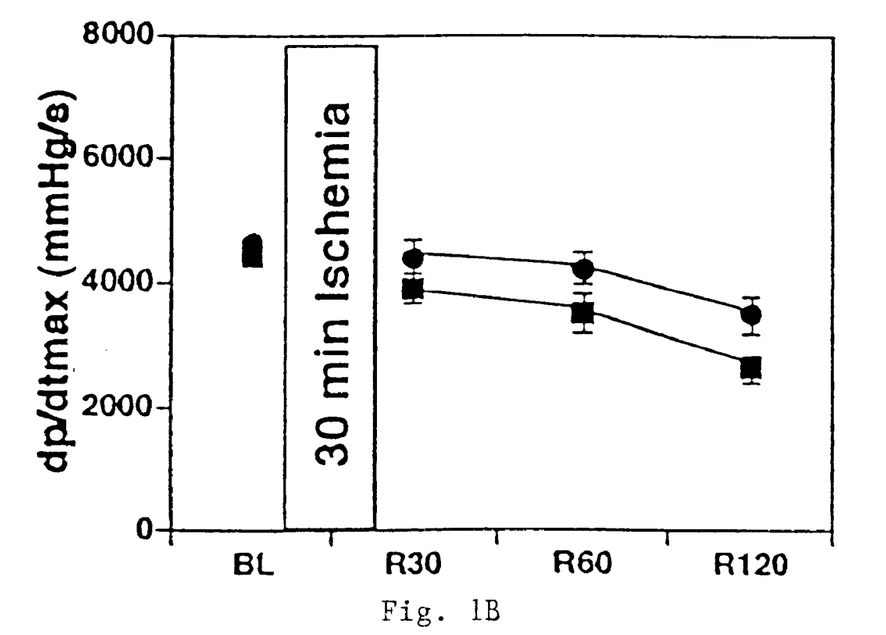
Figure 2A:
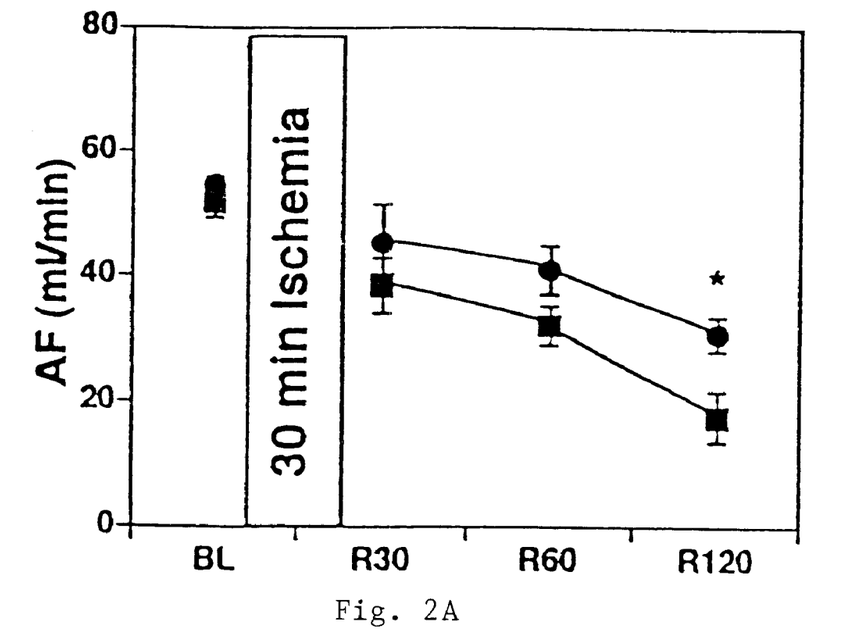
FIGS. 2A and 2B are a graphical representation of aortic flow (2A) and coronary flow (2B) for rats in the control and proanthocyanidin groups. The squares are control data points, and the circles are proanthocyanidin data points. Results are expressed as means ±SEM of six rats per group.
Figure 2B:
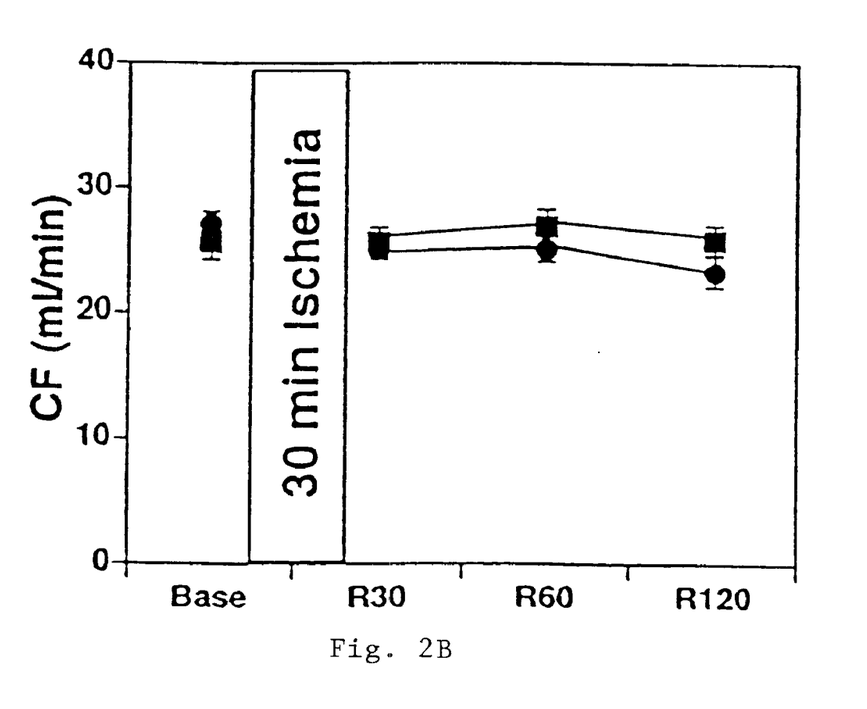

There were no discernable differences in baseline function between control and purified proanthocyanidin composition-fed groups. As was expected, on reperfusion, the absolute values of all functional parameters were decreased in both groups as compared to the baseline values except for aortic pressure and coronary flow which did not exhibit any change. Purified proanthocyanidin composition-fed rat hearts apparently displayed significant recovery of post-ischemic myocardial function. This was evidenced by significant differences in the developed pressure readings throughout the reperfusion period. Significant difference was observed at 120 min of reperfusion (48.5±7.7 mm Hg vs. 73.0±6.1 mm) (FIG. 1A). The maximum first derivative of the developed pressure followed a similar pattern (FIG. 1B). Aortic flow was observed as markedly higher in the proanthocyanidin group from R-60 onwards (FIG. 2A), the difference being significant at R-120 (17.6±4.2 ml/min vs. 30.8±2.7 mL/min). No discernable differences were found for coronary flow (FIG. 2B). Heart rate did not vary significantly between the two groups.

Infarct Size Estimation

Figure 3A:
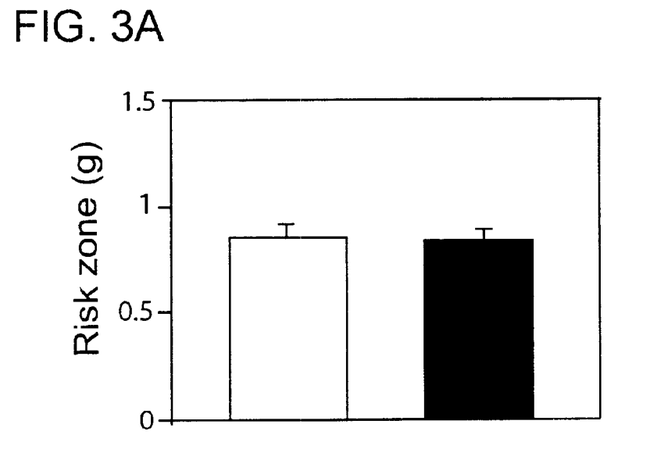
FIGS. 3A–3C are a graphical representation of the size of myocardial infarction after ischemia and reperfusion for rats in the control and proanthocyanidin groups. The squares are control data points, and the circles are proanthocyanidin data points. Results are expressed as means ±SEM of six rats per group.
Figure 3B:
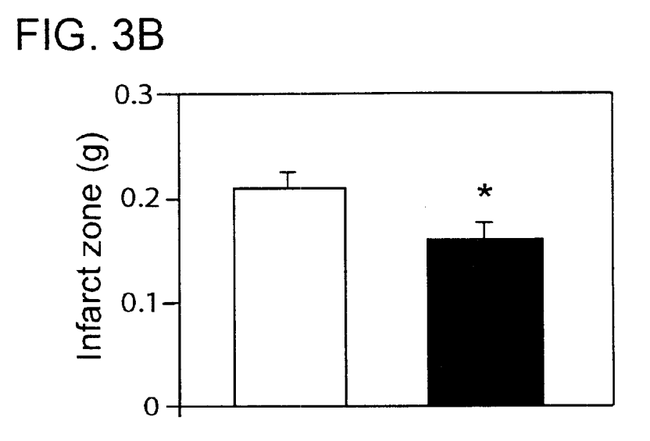
Figure 3C:
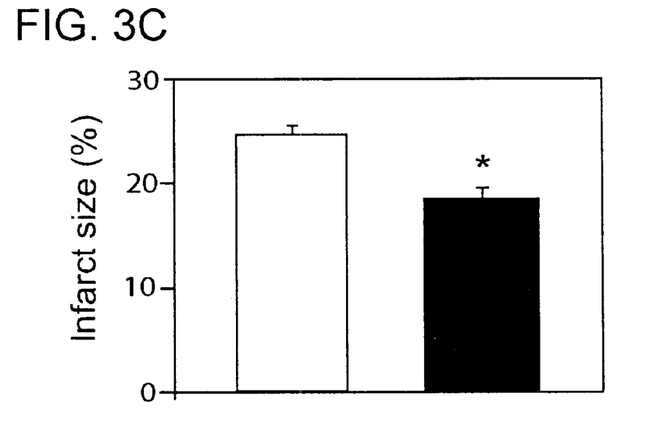
Figure 4A:
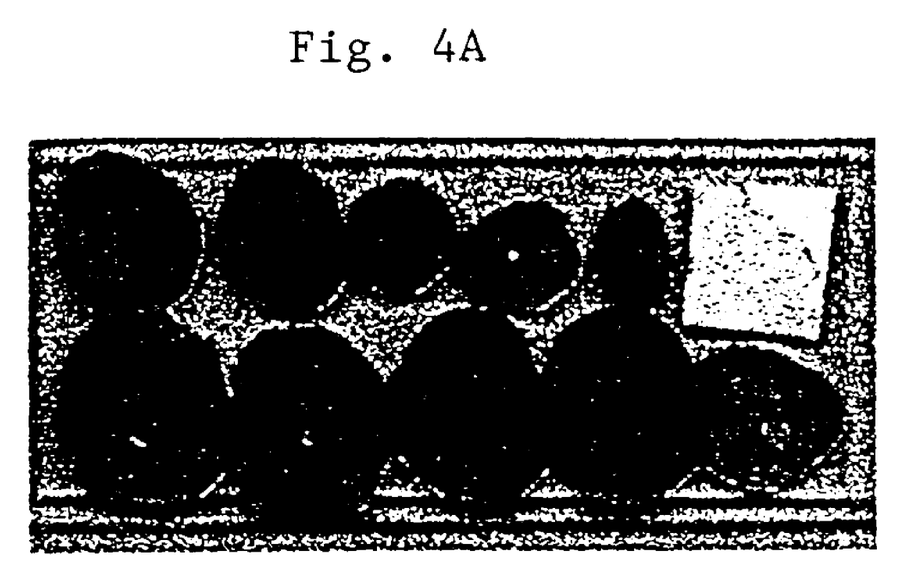
FIGS. 4A and 4B are representative photographs of the infarcts that were quantitated from the control and proanthocyanidin groups.
Figure 4B:
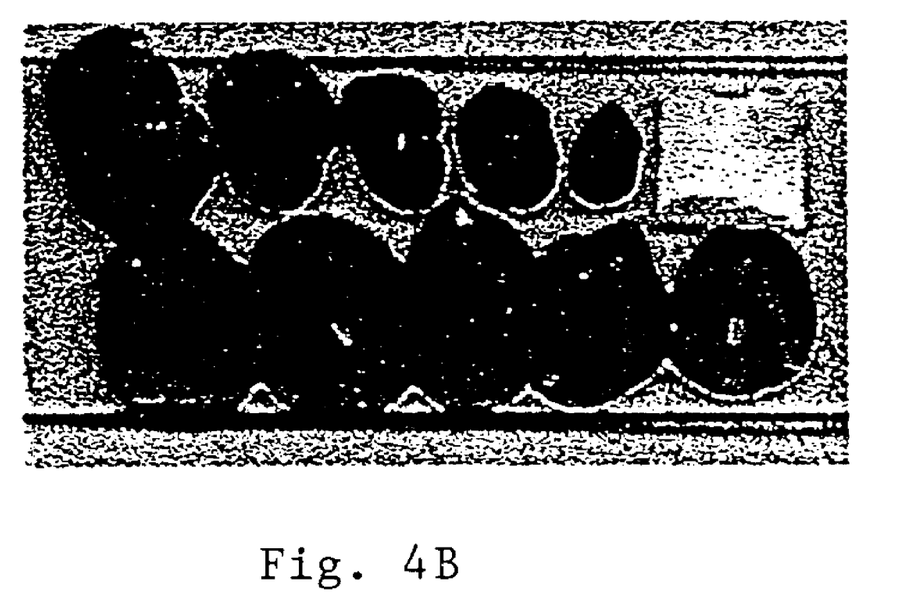

FIGS. 3A–C show that infarct mass and infarct size (% infarct of total volume at risk) were noticeably reduced in the purified proanthocyanidin composition-fed group as compared to the control group (0.209±0.017 gm vs. 0.163±0.012 gm and 24.6±0.8% vs. 18.7±1.0%). A representative photograph of the infarcts that were quantitated is shown in FIGS. 4A and 4B.

Malonaldehyde Assay

Figure 5:
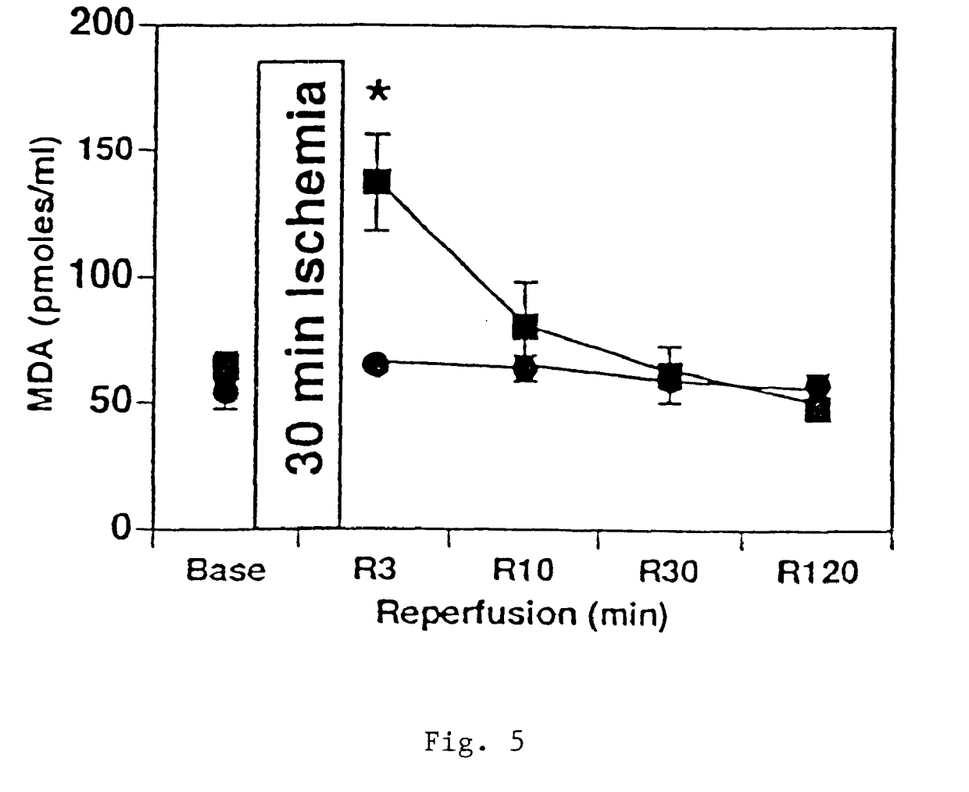
FIG. 5 is a graphical representation of malonaldehyde formation during ischemia and reperfusion for rats in the control and proanthocyanidin groups. The squares are control data points, and the circles are proanthocyanidin data points. Results are expressed as means ±SEM of six rats per group.

Coronary perfusate MDA levels were found to be significantly reduced in the purified proanthocyanidin composition group as compared to the control group (FIG. 5). The difference was especially apparent in the immediate early reperfusion period at R3. Furthermore, at no time during reperfusion were the MDA levels in purified proanthocyanidin composition-fed group significantly elevated above the baseline value.

In Vitro Peroxyl Radical Scavenging Assay

Figure 6:
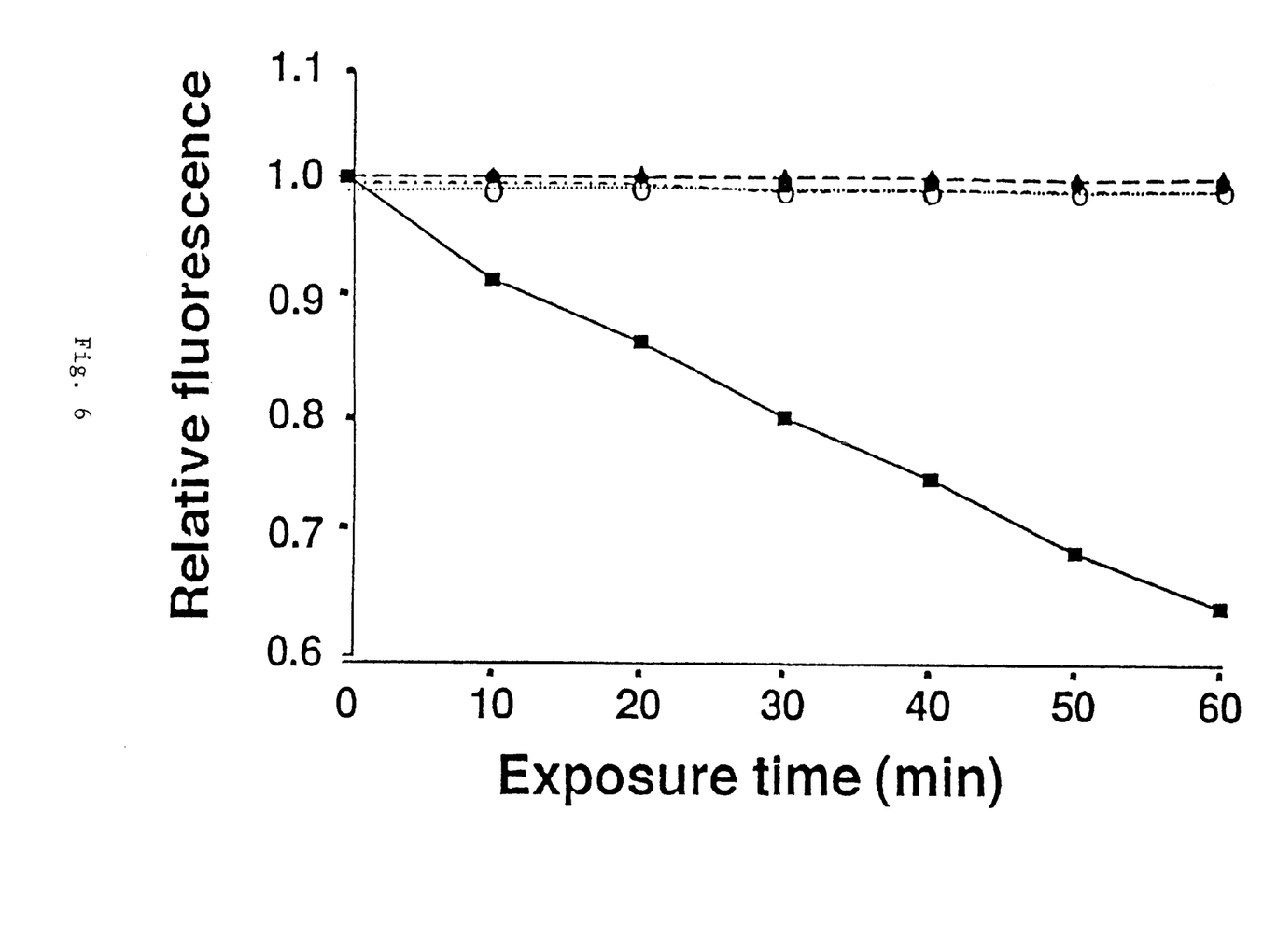
FIG. 6 is a graphical representation of the relative fluorescence obtained by 5-/6-Carboxyfluorescein (5-/6-CF) under various conditions. The triangular data points represent fluorescence obtained by CF (0.1 $\mu$M) alone. The square data points represent fluorescence obtained by CF upon exposure to peroxyl radicals generated by the thermal decomposition of 2,2'-azobis (2-aminopropane) dihydrochloride (AAPH) (2 mM). The open-circle data points represent fluorescence obtained by CF and AAPH with trolox (25 $\mu$g/mL). The filled-circle data points represent fluorescence obtained by CF and AAPH with proanthocyanidin (10 $\mu$g/mL).

The amount of fluorescence of 5-/6-CF decreased when it was exposed for 1 hour to the peroxyl radicals generated by the thermal decomposition of AAPH as shown in FIG. 6. This effect of AAPH was effectively blocked by proanthocyanidin at concentrations of 10 µg/mL. This scavenging activity of proanthocyanidin was comparable with that for 25 µg/mL of trolox.

In Vitro Hydroxyl Radical Scavenging Assay

Figure 7A:
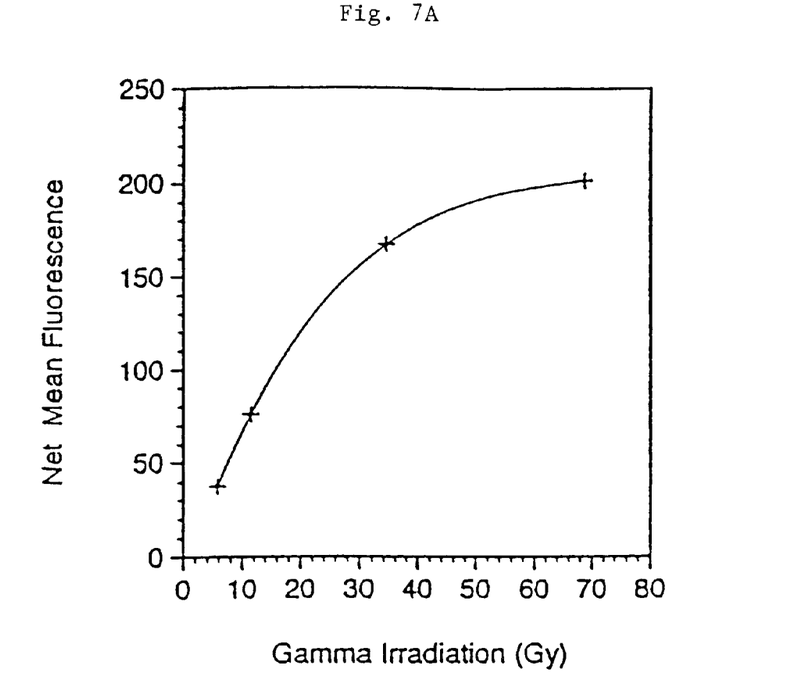
FIG. 7A is a graphical representation of the fluorescence of $10^{-5}$ M aqueous CCA for various doses of absorbed radiation. The excitation was at 400 nm, the emission at 450 nm, and the resolution 5 nm. The radiation was induced at a rate of 1.14 Gy/min.
Figure 7B:
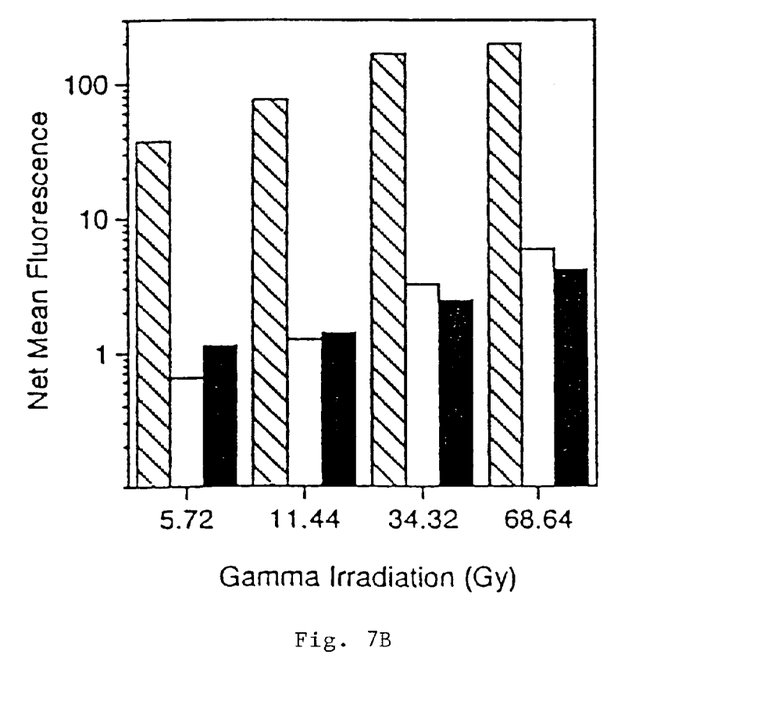
FIG. 7B is a graphical representation of the net mean fluorescence of $10^{-5}$M CCA irradiated under the conditions discussed for FIG. 7A. The hatched bars indicate fluorescence in the absence of proanthocyanidin or DMSO. The solid bars indicate fluorescence in the presence of 10 $\mu$g/mL proanthocyanidin. The unfilled bars indicate fluorescence in the presence of 1 mM DMSO. Results, shown as means, are representative of three experiments per group. Each experiment was run in triplicate.

The induction of 7-OH.-CCA fluorescence by γ-irradiation of CCA is shown in FIG. 7A. With increasing doses of γ-irradiation, the amount of 7-OH.-CCA fluorescence progressively increased, indicating steady formation of OH. The 7-OH-CCA fluorescence was effectively blocked by purified proanthocyanidin composition at a concentration of 10 μg/mL (FIG. 7B). The scavenging activity of the purified proanthocyanidin composition was compared with that for 1 mM DMSO.

Cardiac Apoptosis Markers

The results also showed that administration of the purified proanthocyanidin compositions of the invention reduced apoptotic cardiomyocyte death and DNA laddering and attenuated ischemia/reperfusion-mediated increased abundance of c-Jun and JNK-1 proteins leading to apoptosis. These results suggest that the purified proanthocyanidin products of the invention reduce apoptotic cell death by attenuating the ischemia/reperfusion-induced increased abundance of c-Jun and JNK-1 proteins.

The results of the example demonstrated that purified proanthocyanidin composition-fed animals had greater resistance to myocardial ischemia reperfusion injury than control animals, as evidenced by improved recovery of post-ischemic contractile functions. The purified proanthocyanidin composition-fed group had a reduced extent of myocardial infarction compared to the control group. Purified proanthocyanidin composition-fed rat hearts were more resistant to myocardial ischemic reperfusion injury than hearts obtained from rats whose diet had not been supplemented during 3 weeks prior to the start of the experiment. The purified proanthocyanidin composition-fed group consistently demonstrated better post-ischemic ventricular recovery and reduced myocardial infarction compared to the control group. Flourimetric study demonstrated the antioxidant property of proanthocyanidin as judged by its ability to directly scavenge peroxyl radicals. Taken together, the results of the example indicate that consumption of purified proanthocyanidin composition produces a cardioprotective effect against ischemia reperfusion injury.

Such cardioprotective property may be attributed, at least in part, to the purified proanthocyanidin composition's ability to directly scavenge peroxyl and hydroxyl radicals and to reduce oxidative stress developed during ischemia and reperfusion. On the other hand, proanthocyanidins have been suggested to be potent inhibitors of the enzymes phospholipase A2, cyclooxygenase and lipooxygenase, and these and other biological effects including possible anti-inflammatory effects may alternatively be responsible for the cardioprotective effects of proanthocyanidins. In vitro studies using a peroxyl-radical-generating system by thermal decomposition of AAPH, and an OH radical generating system using γ-irradiation of CCA showed that proanthocyanidin is a potent scavenger of both peroxyl and hydroxyl radicals. However, the etiology of the subendocardial zonal infarctions is uncertain since it was not established that subendocardial reflow was fully established at the onset of reperfusion.

According to this example, a purified proanthocyanidin composition was found to scavenge both hydroxyl and peroxyl radicals. Production of hydroxyl radicals have been confirmed directly by HPLC using electrochemical detection and by ESR spectroscopy (Tosaki et al., "Comparisons of ESR and HPLC methods for the detection of hydroxyl radicals in ischemic/reperfused hearts. A relationship between the genesis of oxygen-free radicals and reperfusion-induced arrhythmias," Biochem. Pharmacol., 45:961–969 (1993)) as well indirectly by the formation of malonaldehyde and 8-OH-DG products (Cordis et al., "Detection of Oxidative Stress in Heart by Estimating the Dinitrophenylhydrazine Derivative of Malonaldehyde," J. Mol. Cell. Cardiol., 27:1645–1653, (1995); Cordis et al., "Detection of Oxidative DNA Damage to Ischemic Reperfused Rat Hearts by 8-Hydroxydeoxyguanosine Formation," Mol. Cell. Cardiol., 30:1939–1944 (1998)). In a previous study, the presence of OH was compared by two different methods (Tosaki et at., "Comparisons of ESR and HPLC methods for the detection of hydroxyl radicals in ischemic/reperfused hearts. A relationship between the genesis of oxygen-free radicals and reperfusion-induced arrhythmias," Biochem. Pharmacol., 45:961–969 (1993)). Isolated buffer-perfused rat hearts were subjected to 30 min of normothermic global ischemia followed by 30 min of reperfusion. 5,5-Dimethylpyrroline-N-oxide (DMPO) was used as a spin-trap agent to detect OH radicals. In additional HPLC studies, salicylic acid was infused into the heart for the detection of OH radicals. In all of these studies, the effects of the hydroxyl radical scavenger, SOD plus catalase on the OH formation were examined. Regardless of the methods used, OH concentration was found to be increased significantly after between 60 and 90 sec of reperfusion, peaking between 120 and 210 sec., and then progressively decreasing. In all cases, SOD plus catalase were able to reduce the formation of OH radicals. Indirectly, a significant number of studies have demonstrated the increased formation of malonaldehyde in the ischemic reperfused myocardium. Recently, a HPLC method was described to monitor the malonaldehyde in the heart that utilized the 2.4-dinitrophenylhydrazine derivatization of the lipid metabolites (Cordis et al., "Detection of Oxidative Sterss in Heart by Estimating the Dinitrophenylhydrazine Derivative of Malonaldehyde," J. Mol. Cell Cardiol., 27:1645–1653 (1995)). The results of the present example demonstrated an increase in malonaldehyde production in the control group during early reperfusion supporting previous reports concerning an increased formation of lipid peroxidation products during the reperfusion.

The results of the example showed that purified proanthocyanidin composition exerts an antioxidant effect on the ischemic reperfused myocardium. Antioxidant reserve and antioxidant enzymes are significantly reduced after ischemia and reperfusion. For example, reduced amount of SOD, catalase, and glutathione peroxidase enzymes as well as α-tocopherol and ascorbic acid have been found in the ischemic reperfused myocardium (Hearse, Marcel Dekker, 7–17, Roberts A J ed., New York (1987); Das et al., "Pathophysiology of Superoxide Radical as Potential Mediator of Ischemic and Reperfusion Injury in Pig Heart," Basic Res. Cardiol., 81:155–166 (1986)). The loss of key antioxidant enzymes and antioxidants thus reduces the overall antioxidant reserve of the heart, and makes the heart susceptible to ischemia/reperfusion injury. One of the major functions of antioxidants is to reduce free radical formation. Thus, the reduced antioxidative defense is likely to be incapable of providing complete protection against increased activities of the reactive oxygen species.

The results of the example demonstrate that the purified proanthocyanidin composition scavenged both hydroxyl and peroxyl radicals that are generated in the ischemic reperfused myocardium. In this system, OH was generated by ionizing radiation (Roots et al., "Estimation of Life Times and diffusion Distances of Radicals Involved in X-ray Induced DNA Strand Breaks or Killing of Mammalian Cells," Radiat. Res., 64:306–320 (1975)). OH plays a crucial role in myocardial ischemic reperfusion injury (Tosaki et al., "Comparisons of ESR and HPLC methods for the detection of hydroxyl radicals in ischemic/reperfused hearts. A relationship between the genesis of oxygen-free radicals and reperfusion-induced arrhythmias," Biochem. Pharmacol., 45:961–969 (1993)). In spite of their relatively low oxidizing ability compared to OH radicals, in biological systems, organic peroxyl radicals could be extremely damaging to the issues (Chance et al., "Hydroperoxide Metabolism in Mammalian Organs," *Physiol. Res.,* 59:527–540 (1979)). Tissues such as those in the heart are protected from the detrimental actions of peroxyl radicals by the presence of naturally occurring antioxidants, such as bilirubin and biliverdin, as well as plasma antioxidants (Frei et al., "Antioxidant Defences and Lipid Peroxidation in Human Blood Plasma," *Proc. Natl. Acad. Sci.,* 85:9748–9751 (1988)). Ascorbic acid and vitamin E comprise the other potent peroxyl radical traps for the biological systems (Stocker et al., "Synergistic Interaction Between Vitamin E and the Bile Pigments Bilirubin and Biliverdin," *Biochim. Biophys. Acta.,* 1002:238–244 (1989)). Generally, lipid soluble antioxidants can scavenge chain-carrying lipid peroxyl radicals thereby preventing propagation of lipid peroxidation after the initiation of the lipid peroxidation. The results of the example demonstrated that not only did proanthocyanidin scavenge the hydroxyl and peroxyl radicals, it also reduced the extent of lipid peroxidation in the ischemic reperfused myocardium. These findings are important because peroxyl radicals are known to be formed in vivo in membranes and lipoproteins as intermediate products of lipid peroxidation. The potent peroxyl and hydroxyl radical scavenging ability of purified proanthocyanidin composition makes it a useful dietary supplement to reduce ischemia reperfusion injury.

In view of these results, administering purified proanthocyanidin composition to patients who are at risk for ischemic reperfusion injury will serve as an effective method for prevention of such injury. Administration of prior to reperfusion also is believed to help prevent reperfusion injury. The method involves identification of those prone to such injury, such as those with or at high risk for blocked arteries, and administration of purified proanthocyanidin composition to the identified persons in an amount sufficient to prevent or reduce the injury. Though the preferred method of administration is oral, various known methods for administering compounds to a person would also be effective. In the example previously detailed, 100 mg/day per kg of body weight was found to be effective in reducing reperfusion injury in rats. This is equivalent to a dose of 164 mg of purified proanthocyanidin composition per day for a 70 kg adult human. Based on these results and other in vivo studies, a preferred daily dose to prevent injury is roughly 100–200 mg of purified proanthocyanidin composition, preferably in two equally divided doses taken after meals. If purified proanthocyanidin composition is taken post- rather than pre-reperfusion, a somewhat higher dose may be effective.

Additionally, a composition comprising purified proanthocyanidin composition and an artificial blood substitute will be effective in preventing or reducing reperfusion injury caused by administration of the blood substitute. The composition includes a sufficient concentration of purified proanthocyanidin composition to be effective in preventing or reducing reperfusion injury.

Although the invention has been disclosed in detail with reference only to the preferred embodiments, those skilled in the art will appreciate that additional methods of administering purified proanthocyanidin composition can be made without departing from the scope of the invention. Accordingly, the invention is defined only by the following claims.

We claim:
1. A composition comprising:
   a purified proanthocyanidin composition in an amount effective to prevent or reduce ischemic reperfusion injury; and
   an artificial blood substitute inducing the ischemic reperfusion injury upon introduction into the body of a person.

* * * * *